(12) United States Patent
Stephan et al.

(10) Patent No.: US 8,257,606 B2
(45) Date of Patent: Sep. 4, 2012

(54) CERAMIC BODY AND PROCESS FOR THE PREPARATION THEREOF

(75) Inventors: Marc Stephan, Lörrach (DE); André Schöne, Bad Säckingen (DE)

(73) Assignee: Vita Zahnfabrik H. Rauter GmbH & Co. KG, Bad Säckingen (DE)

(*) Notice: Subject to any disclaimer, the term of this patent is extended or adjusted under 35 U.S.C. 154(b) by 25 days.

(21) Appl. No.: 12/667,755

(22) PCT Filed: Jul. 7, 2008

(86) PCT No.: PCT/EP2008/058763
§ 371 (c)(1),
(2), (4) Date: Jan. 5, 2010

(87) PCT Pub. No.: WO2009/007338
PCT Pub. Date: Jan. 15, 2009

(65) Prior Publication Data
US 2010/0178636 A1    Jul. 15, 2010

Related U.S. Application Data

(60) Provisional application No. 60/935,164, filed on Jul. 30, 2007.

(30) Foreign Application Priority Data

Jul. 6, 2007  (EP) .................................... 07111886

(51) Int. Cl.
*B44C 1/22* (2006.01)
(52) U.S. Cl. ............. 216/96; 216/83; 433/173; 433/215
(58) Field of Classification Search .................... 216/83, 216/96, 88; 433/173, 215
See application file for complete search history.

(56) References Cited

U.S. PATENT DOCUMENTS
4,123,591 A * 10/1978 Karki .............................. 428/454
(Continued)

FOREIGN PATENT DOCUMENTS
DE        4138214 A1    5/1993
(Continued)

OTHER PUBLICATIONS

Canay et al., "Effect of different acid treatments on a porcelain surface", Journal of Oral Rehabilitation, 28(1):95-101 (Jan. 2001).

(Continued)

*Primary Examiner* — Shamim Ahmed
(74) *Attorney, Agent, or Firm* — Dardi & Herbert, PLLC; Curtis B. Herbert

(57) ABSTRACT

A process for the preparation of ceramic dental implants having a surface for improving osseointegration, wherein the following process steps are performed for preparing such surface: —preparation of a ceramic blank having a surface; —treating at least one partial area of the surface of the ceramic blank by an ablating process that produces a surface roughness of the surface that corresponds to a treatment by sand blasting under a blasting pressure of from 1.5 bar to 8 bar and with a grain size of the blasting media used for sand blasting of from 30 μm to 250 μm; —followed by a chemical treatment of said at least one partial area of the surface of the ceramic blank treated with the ablating process; —followed by a thermal treatment of the blank whose surface has been subjected to said ablating and chemical treatments at temperatures of >125° C. > A ceramic body obtainable by the process according to the invention is also described.

Figure 1A:
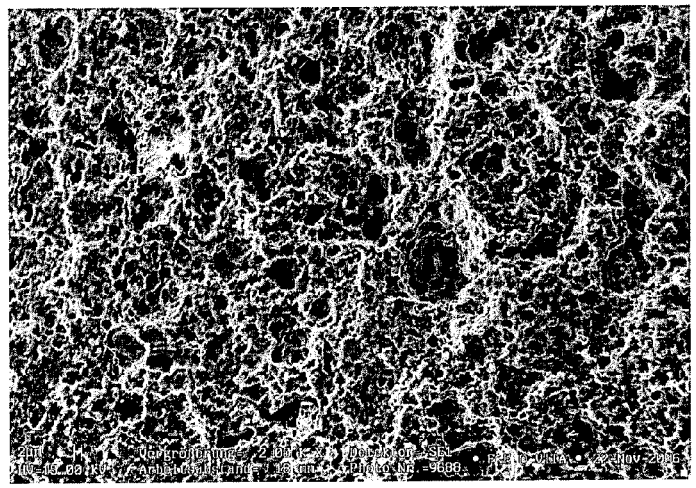

16 Claims, 2 Drawing Sheets 2,000 x magnification

U.S. PATENT DOCUMENTS

| | | | |
|---|---|---|---|
| 5,578,349 A | 11/1996 | Koshkarian et al. | |
| 6,296,716 B1 | 10/2001 | Haerle et al. | |
| 2003/0019843 A1* | 1/2003 | Kawai et al. | 216/108 |
| 2003/0059742 A1* | 3/2003 | Webster et al. | 433/201.1 |
| 2003/0108658 A1* | 6/2003 | Andersch et al. | 427/2.1 |
| 2005/0106534 A1* | 5/2005 | Gahlert | 433/173 |

FOREIGN PATENT DOCUMENTS

| | | |
|---|---|---|
| WO | 2006/131010 A2 | 12/2006 |

OTHER PUBLICATIONS

Hofer: Heissisostatisches Pressen, Section 9.3, p. 179.

Kriegesmann, Keramische Werkstoffe, Chapter 3.6.3.0, Jan. 1993, (22 pages).

Kruse et al., Technologie der Keramik-I, vol. 2: Mechanische Prozess (1982) pp. 191-193.

* cited by examiner 2,000 x magnification 10,000 x magnification 2,000 x magnification 10,000 x magnification

CERAMIC BODY AND PROCESS FOR THE PREPARATION THEREOF

RELATED APPLICATION

This application is national stage filing of PCT Application No. PCT/EP2008/058763 filed Jul. 7, 2008, which claims priority to European Patent Application No. 07111886.3 filed Jul. 6 2007 and U.S. Provisional Application No. 60/935,164 filed Jul. 30, 2007, each of which are hereby incorporated herein by reference.

TECHNICAL FIELD OF THE INVENTION

The present invention relates to a ceramic body, a process for the preparation thereof, and the use of said ceramic body, especially in medicine.

INTRODUCTION TO THE INVENTION

Technical ceramics or high-performance ceramics have a number of properties that can be utilized to improve products in numerous applications in machine and equipment construction, in process and production technology, in hightemperature applications, in precision technology, electrotechnology and electronics and in optics. Some processes become even possible only by the use of high-performance ceramics. Such properties include:

Refractoriness and thermal shock resistance, high strengths and reliability, also in the range of high temperatures, low coefficient of thermal expansion, hardness and abrasion resistance, resistance against chemical corrosion, low density, maximum rigidity, long-term strength (no fatigue).

If employed in a competent way, such materials can achieve economic advantages for the user as compared to traditional materials (metals, plastic materials, glass and conventional ceramics), for example, by a prolonged service life of components and aggregates or by an improvement of the efficiency of reactions due to the application of higher temperatures. Limitations of the use of ceramic materials, for example, due to their brittleness, can be avoided by using a construction that takes the specific requirements of ceramics into account.

Therefore, ceramic bodies are employed in quite a lot of fields of technology. As fields of application in addition to technical fields, there may be mentioned, in particular, medicine and dental medicine, where ceramics are employed for implants. In this function, they compete with metals, such as titanium. However, it has not been possible to date to provide ceramic implants with surface topologies similar to those of titanium implants, which may have negative effects on the implant integration and healing process.

Previous ceramic implants have machined or sand-blasted surfaces. Especially sand-blasted surfaces do not have optimum mechanical and microbiological properties due to the sharp-edged surface damage and the superficial residues of the blasting medium.

Surfaces of ceramics can be treated in different ways.

DE-A-41 38 214 relates to a process for the high-adhesion metallization of aluminum nitride ceramics. In this process, the ceramics is mechanically pretreated, cleaned and chemically aftertreated, whereby a uniform fine roughening is achieved. This enables a very high adhesion anchoring of a later applied two-step metallization.

U.S. Pat. No. 6,296,716 relates to a cleaning method for ceramic workpieces, such as silicon carbide boats as employed in semiconductor production. The process includes the washing of a virgin or used ceramic workpiece with a strong acid, followed by using a pelletized $CO_2$ cleaning process on the acid-cleaned workpiece.

U.S. Pat. No. 5,578,349 relates to a process for applying a uniformly adherent tantalum oxide protective layer to a portion of a ceramic glow plug for protecting the glow plug from corrosive environmental conditions generated by the combustion of alternative fuels in a diesel engine. The coating is effected by depositing tantalum oxide on a silicon nitride glow plug by plasma spray-deposition techniques.

WO-A-2006/131010 relates to a ceramic implant, especially a dental implant, having a structured or porous surface for at least partial insertion into a bone. A particularly advantageous porous surface is obtained if it is modified in a salt melt at least in areas thereof. These excellent osteointegration properties can be caused in a process in which the surface is surface-modified in a salt melt at least in the areas exposed to bones and/or soft tissue, optionally after a previous ablating surface modification.

In the Journal of Oral Rehabilitation, 2001, 28; 95-101, S. Canay et al. report a study for determining effects of selected surface treatments on the surface structure of a feldspar porcelain. Three different etching treatments with different acids were examined.

DESCRIPTION OF THE INVENTION

One object of the present invention is to provide a ceramic surface that avoids the drawbacks of the prior art. In particular, the ceramic surface is supposed to enable the growth and bonding of bone tissue and improve the integration and healing process when used in medical implants. In particular, a shortening of the healing time (time to loading) of ceramic implants is to be achieved, so that they can be subjected to full load earlier. Another object is to provide a process for the preparation of ceramic surfaces.

The object is achieved by a process for the preparation of ceramic dental implants having a surface for improving osseointegration, wherein the following process steps are performed for preparing such surface:

preparation of a ceramic blank having a surface;
treating at least one partial area of the surface of the ceramic blank by an ablating process that produces a surface roughness of the surface that corresponds to a treatment by sand blasting under a blasting pressure of from 1.5 bar to 8 bar and with a grain size of the blasting media used for sand blasting of from 30 µm to 250 µm;
followed by a chemical treatment of said at least one partial area of the surface of the ceramic blank treated with the ablating process;
followed by a thermal treatment of the blank whose surface has been subjected to said ablating and chemical treatments at temperatures of >125° C.

The blank that can be employed in the process according to the invention may, but need not, have a defined shape, such as the shape of a dental implant or the like.

The invention enables the production of a nanostructures microtopography appropriate for the material involved by the combination of the individual process steps. The chemical treatment opens up degrees of freedom that may be utilized for adjusting the surface topography and properties. The thermal aftertreatment causes an additional etching effect, the so-called thermal etching, so that oxides admixed for adjusting desired properties can diffuse into crystallographically/energetically favorable positions of the crystal lattices and leave a nanostructures surface without "sharp" edges. This applied, for example, to zirconium oxides, in which a microtopography without the formation of the undesirable zirconium fluorides can be achieved by adjusting the time of chemical etching. One advantage is the faster biological integration of an implants into the bone that can be expected with such a surface.

The preparation of the ceramic blank is effected, for example, by forming processes, such as isostatic pressing, to obtain a precursor blank that is compacted by sintering, especially atmospheric sintering and/or hot isostatic pressing. In addition to atmospheric sintering, sintering under a gas atmosphere of a different kind, such as in the presence of hydrogen, may also be used to provide different properties. Further, uniaxial pressing, ceramic injection molding and low-pressure injection molding may be used as processes for the preparation of the precursor blank. The oxidic components that are usually employed for the preparation of a ceramic blank are subjected to the forming processes in a powderized form. The relevant processes are described, for example, in E. Kruse et al.: Technologie der Keramik-I, Volume 2: Mechanische Prozesse (1982), for dry pressing and isostatic pressing and in J. Kriegesmann: Keramische Werkstoffe, Chapter 3.6.3.0; B. W. Hofer, Heiβisostatisches Pressen (1993), for hot isostatic pressing. The precursor blank may then be surface-treated if its strength is sufficient to withstand the mechanical surface treatment process.

The oxidic components include, in particular, oxides of the metals aluminum, zirconium, yttrium, cerium, hafnium, magnesium and, in low proportions, also iron, lanthanum, chromium, strontium, silicon, calcium.

The size of the particles that can be employed in the process according to the invention is not critical since all sizes that are usual in ceramics production can be employed. Typically, the particle size is within a range of from 0.1 µm to 3 µm, especially from 0.3 µm to 1 µm.

In one embodiment of the process according to the invention, the ceramic blank is compacted in this process step to a density of ≧90% to 99.9% of the theoretical density (100% pore-free).

If the coloring obtained after the process step of precursor blank production is undesirable, a so-called white heat calcination may be recommendable. "White heat calcination" means the sintering or annealing of ceramics in an oxidative atmosphere after hot isostatic pressing. The prepared ceramic blank can be processed by ablating processes for further forming. As the ablating process, there may be used, for example, grinding, milling, laser ablation processes and/or polishing.

In a further step of the process according to the invention, the ceramic blank prepared as described above and optionally brought into a desired shape by ablating processes is further processes in an ablating process step. The mechanical process step for processing the surface of the ceramic blank ultimately causes a higher roughness of the surface of the ceramic blank. It is sufficient to roughen the portion of the blank that is to be anchored in the bone, and optionally the neck of the implant.

As the mechanical process step according to the invention, there may be used, for example, a material blasting process, such as a grinding process, milling and/or laser ablation process. The process according to the invention can be performed, in particular, by material blasting processes by means of hard particles, such as corundum, diamond, silicon carbide. The particle size of the hard particles may be from 1 µm to 250 µm.

A sand blasting process has proven useful, in particular. Sand blasting can be performed under a blasting pressure of from 1.5 bar to 8 bar, or even 2.5 bar to 8 bar or more depending on the grain size of the blasting media or its condition, especially from 4 bar to 6 bar. In particular, $Al_2O_3$ is used as the blasting medium. The grain size of the blasting medium, especially $Al_2O_3$, is from 30 µm to 250 µm, especially from 30 µm to 130 µm.

According to the invention, the mechanical treatment is followed by a chemical treatment. According to the invention, the chemical treatment is effected, for example, by etching the surface of the ceramic blank by treatment with hydrofluoric acid, solutions containing hydrofluoric acid, nitric acid, sulfuric acid and/or salt melts. Typically, said solutions containing hydrofluoric acid are HF in water. U.S. Pat. No. 6,969, 688 describes solvents and a halogen-containing acid, the solvent including at least one of the following components: $H_2O$, alcohol, tetrahydrofuran (THF), sulfuric acid ($H_2SO_4$) and dimethyl sulfoxide (DMSO), and the halogen-containing acid including at least one of the following components: HF, HBr, HI and $HClO_4$.

As etching agents in the process according to the invention, as salt melts there may be used, for example, those mentioned in WO-A-2006/131010. According to a first preferred embodiment of the process, the salt melt is a salt melt of alkali and/or alkaline earth nitrates, alkali and/or alkaline earth hydroxides or alkali and/or alkaline earth halides, or a mixture of such salts. The salt melt may comprise at least one hydroxide, especially an alkali and/or alkaline earth hydroxide. As (eutectic) salt melts, there may be employed those that exclusively consist of one or several hydroxides, especially of one or several alkali and/or alkaline earth hydroxides. The mixtures may be binary, ternary or even higher. In particular, a salt melt essentially consisting of alkali hydroxides, such as potassium hydroxide and/or sodium hydroxide and/or lithium hydroxide, is used. Minor components, typically in a range of less than 5% or even less than 2%, of other salts or other additives, whether for adjusting the etching activity of for adjusting the melt temperature, may additionally be present.

For example, there may be employed binary salt melts, for example, of potassium hydroxide and sodium hydroxide, the two components being present in a ratio of from 2:1 to 0.5:1, especially within a range of from 1.5:1 to 0.75:1. With such binary salt melts, especially consisting of the mentioned components, the process is performed, for example, at a temperature within a range of from 100 to 600° C., especially at a temperature within a range of from 150 to 250° C.

For example, ternary salt melts of potassium hydroxide, sodium hydroxide and lithium hydroxide also prove to be useful, these three components being used in a ratio within a range of 10-20:4-10:0.5-2, especially within a range of 14:6: 1. With such ternary salt melts, the process may be performed at a temperature of from 100 to 400° C., especially at a temperature within a range of from 150 to 250° C.

In general, it may be said that a salt melt may typically be used at a temperature within a range of from 80 to 1300° C., especially within a range of from 150 to 600° C.

At least in particular areas, the surface to be processed is exposed to a salt melt, for example, in the form of a bath, over a period of from 10 minutes to 300 hours or from 10 to 100 hours, especially from 25 to 35 hours. However, other times, preferably at least one hour, may also be used depending on the results to be obtained.

Using the duration of exposure of the blank to the etching medium, the condition of the surface can be adjusted, for example. Thus, when fluorine-containing acids, such as hydrofluoric acid, act for a short period of time, the formation of remarkable amounts of zirconium fluorides is suppressed. If desired, partial areas may be excluded from etching, for example, by avoiding contact thereof with the etching agent or covering the surface of such partial areas with substances that withstand contact with the etching agent, for example, wax, PE, PP.

Following the mechanical and chemical treatment of the surface of the ceramic blank, the process according to the invention provides for a thermal treatment.

The thermal treatment is typically effected at temperatures of from 900° C. to 1500° C., especially from 1200° C. to 1400° C.

According to the invention, the process is conducted, for example, under an oxidative atmosphere. The holding times at the desired end temperature are from 1 h to 5 h, in particular.

The thermal treatment is effected after the mechanical and chemical treatments, wherein the steps of the process according to the invention can be performed after preparation processes of the ceramic blank. The mechanical processing can be performed before the hot isostatic pressing, followed by mechanical processing and chemical treatment by the process according to the invention. The thermal treatment may also be coincident with the hot isostatic pressing. Also, the process of blank preparation and surface modification may be effected between the hot isostatic pressing and the white heat calcination. Thus, the white heat calcination would be the same as the concluding thermal process.

The invention also relates to a ceramic body with a surface that can be obtained by the process according to the invention. The ceramic body according to the invention has a singular surface that may be interpreted as a superposition of a microstructured surface introduced by the mechanical treatment, and a nanostructured surface. Typically, the roughness (Ra) values of the surface are within a range of from 0.5 µm to 2.5 µm, especially from 0.9 µm to 1.8 µm.

The ceramic body according to the invention may be used, for example, in a form designed as a medicinal implant. In particular, devices such as dental implants, endoprostheses, bone nails, bone screws (cortical screws) and plates may be mentioned. The ceramic bodies according to the invention may also be employed as an active surface, such as supports for catalysts, filters and adsorption material.

The roughnesses formed by the process according to the invention were established with a Hommel Tester T8000 surface roughness measuring device (caliper with a diamond tip of 2 µm radius and 60° opening angle). The Ra values measured are within a range of from 0.5 µm to 2.5 µm, especially within a range of from 0.9 µm to 1.8 µm.

The invention will be further explained illustratively in the following.

EXAMPLE 1

A sample of 3Y-TZP-A was presintered at 1350° C., and its surface was subsequently sand-blasted with 130 µm corundum powder under a pressure of 6 bar and at a blasting distance of 4 cm. After the sample had been cleaned, it was etched in 38-40% hydrofluoric acid for 8 hours. Finally, the sample was watered, dried and resintered at 1500° C. for one hour.

With a Hommel Tester T8000 surface roughness measuring device and a caliper with a diamond tip (2 µm radius and 60° opening angle), the resulting surface roughness was determined (DIN EN ISO 4287). The measuring speed was 0.15 mm/s:

$R_a$=2.11 µm; $R_z$=15.56 µm; $R_t$=19.43 µm, and $R_{max}$=18.51 µm

Figure 1B:
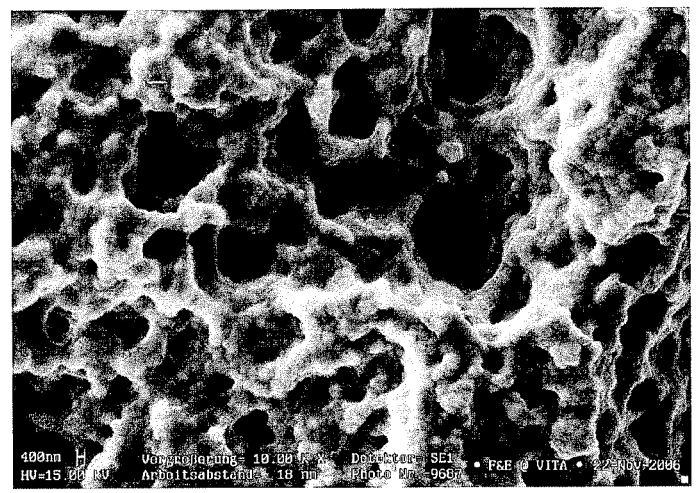

FIGS. 1a and 1b show the surfaces obtained in 2000× and 10,000× magnification, respectively.

EXAMPLE 2

A sample of 3Y-TZP-A was presintered at 1350° C. After the sample had been cleaned, it was etched in 38-40% hydrofluoric acid for 8 hours. Finally, the sample was watered, dried and resintered at 1500° C. for one hour.

With a Hommel Tester T8000 surface roughness measuring device and a caliper with a diamond tip (2 µm radius and 60° opening angle), the resulting surface roughness was determined (DIN EN ISO 4287). The measuring speed was 0.15 mm/s:

$R_a$=1.86 µm; $R_z$=15.82 µm; $R_t$=18.64 µm, and $R_{max}$=17.93 µm

Figure 2A:
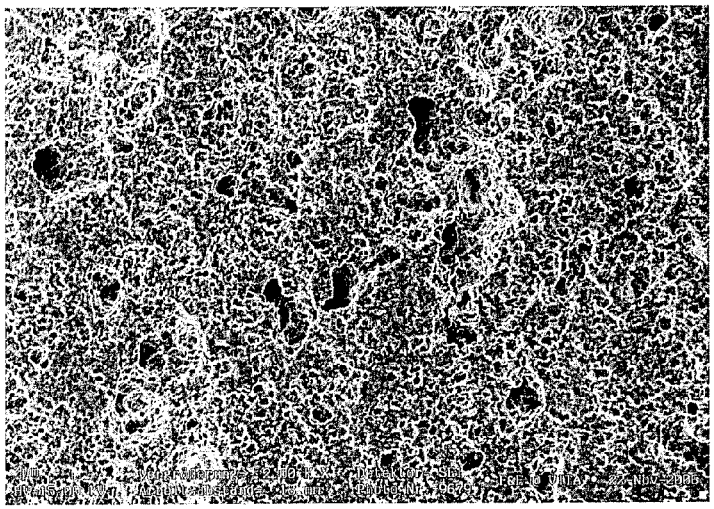
Figure 2B:
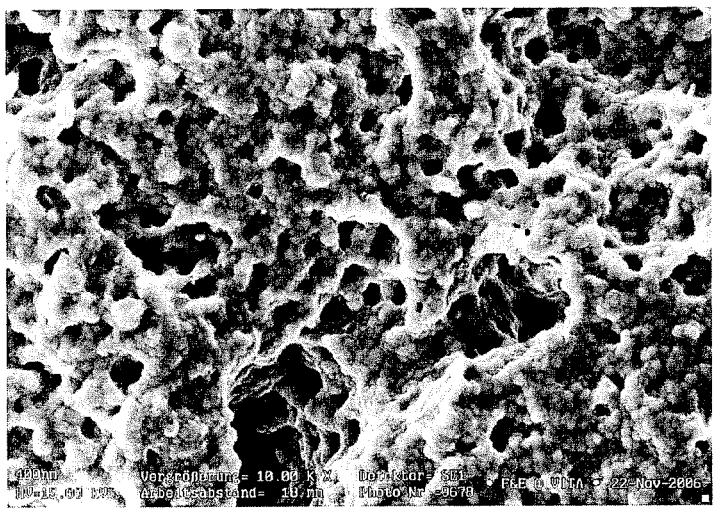

FIGS. 2a and 2b show the surfaces obtained in 2000× and 10,000× magnification, respectively.

EXAMPLE 3

A sample of Y-TZP-A was presintered at 1500° C., and its surface was subsequently sand-blasted with 50 µm corundum powder under 6 bar and at a blasting distance of 4 cm. After the sample had been cleaned, it was etched in 38-40% hydrofluoric acid for 1 hour. Finally, the sample was watered, dried and resintered at 1400° C. for one hour.

With a Hommel Tester T8000 surface roughness measuring device and a caliper with a diamond tip (2 µm radius and 60° opening angle), the resulting surface roughness was determined (DIN EN ISO 4287). The measuring speed was 0.15 mm/s:

$R_a$=0.935 µm; $R_z$=6.786 µm; $R_{max}$=7.803 µm

The invention claimed is:

1. A process for the preparation of ceramic dental implants having a surface for improving osseointegration, with preparing such a surface comprising:
    preparation of a ceramic blank for a dental implant having a surface;
    treating at least one partial area of the surface of the ceramic blank by an ablating process that produces a surface roughness of the surface that corresponds to a treatment by sand blasting under a blasting pressure of from 1.5 bar to 8 bar and with a grain size of the blasting media used for sand blasting of from 30 µm to 250 µm;
    followed by a chemical treatment of said at least one partial area of the surface of the ceramic blank treated with the ablating process;
    followed by a thermal treatment of the blank whose surface has been subjected to said ablating and chemical treatments at temperatures of greater than 125° C.

2. The process according to claim 1, wherein the preparation of the ceramic blank is effected by forming processes to obtain a precursor blank that is compacted by a member of the group consisting of sintering hot isostatic pressing, ceramic injection molding, low-pressure injection molding, and combinations thereof.

3. The process according to claim 1, wherein said ceramic blank is compacted to a density of at least 90% of a theoretical density.

4. The process according to claim 1, wherein white heat calcination is effected after the ceramic blank has been prepared.

5. The process according to claim 1, wherein said ablating process is a member of the group consisting of grinding, milling, a laser ablation process, polishing, and combinations thereof.

6. The process according to claim 1, wherein said mechanical process for processing the surface of the ceramic blank causes a higher roughness of the surface of the ceramic blank.

7. The process according to claim 6, wherein said ablating process is a material blasting process and/or grinding process.

8. The process according to claim 6, wherein said ablating process is performed with hard particles chosen from the group consisting of corundum, diamond, and silicon carbide.

9. The process according to claim 6, wherein the particle size of the hard particles is from 1 µm to 250 µm.

10. The process according to claim 6, wherein said ablating process comprises sand blasting under a blasting pressure of from 1.5 bar to 8 bar and the blasting medium, being employed with a grain size of from 30 µm to 250 µm.

11. The process of claim 1, wherein said chemical treatment of the surface of the ceramic blank before or after the mechanical processing of the surface of the ceramic blank comprises etching the surface of the ceramic blank.

12. The process according to claim 11, wherein said etching of the surface of the ceramic blank comprises a treatment chosen from the group consisting of (i) hydrofluoric acid, (ii) solutions that comprise hydrofluoric acid, nitric acid, sulfuric acid, HBr, HI, or $HClO_4$, and (iii) solvents and/or salt melts of the same.

13. The process according to claim 12, wherein said solutions containing hydrofluoric acid are HF in water.

14. The process according to claim 12, wherein said salt melts are chosen from the group consisting of alkali and/or alkaline earth nitrates, alkali and/or alkaline earth hydroxides, alkali and/or alkaline earth halides, and a mixture of such salts.

15. The process of claim 1, wherein said thermal treatment following said mechanical and chemical treatments of the surface of the ceramic blank is performed at temperatures of from 900° C. to 1500° C.

16. The process according to claim 15, wherein the subsequent thermal treatment is conducted under an oxidative atmosphere with holding times at the end temperature of from 1 h to 5 h.

* * * * *